United States Patent [19]

Sadler, III et al.

[11] 3,992,327

[45] Nov. 16, 1976

[54] CATALYSTS AND ADSORBENTS HAVING HIGH SURFACE AREA TO WEIGHT

[75] Inventors: Leon Y. Sadler, III; William J. Hatcher, Jr., both of Tuscaloosa, Ala.

[73] Assignee: The United States of America as represented by the Secretary of the Interior, Washington, D.C.

[22] Filed: Nov. 11, 1974

[21] Appl. No.: 522,829

[52] U.S. Cl. .............................. 252/449; 252/477 R
[51] Int. Cl.² ..................... B01J 21/08; B01J 29/00
[58] Field of Search ................ 252/449, 451, 477 R; 423/335

[56] References Cited
UNITED STATES PATENTS

| | | | |
|---|---|---|---|
| 1,760,289 | 5/1930 | Stoewener et al. ................. | 252/451 |
| 2,390,490 | 12/1945 | Atwell .............................. | 252/449 X |
| 2,973,246 | 2/1961 | Harman et al. ..................... | 423/335 |
| 3,070,426 | 12/1962 | Winyall ............................. | 423/335 |
| 3,231,518 | 1/1966 | Church .............................. | 252/449 |

*Primary Examiner*—Carl F. Dees
*Attorney, Agent, or Firm*—Roland H. Shubert; Donald R. Fraser

[57] ABSTRACT

Catalysts or adsorbents having high surface-to-weight ratios prepared by attrition grinding are described. This grinding technique enables materials which have a low surface area-to-weight ratio and hence have lesser activity as catalysts or adsorbents, to acquire a large surface to weight ratio which could not be achieved by chemical precipitation means. Exemplary of these materials are naturally occuring crystalline α-quartz and manganese doped aluminum oxide.

4 Claims, 2 Drawing Figures

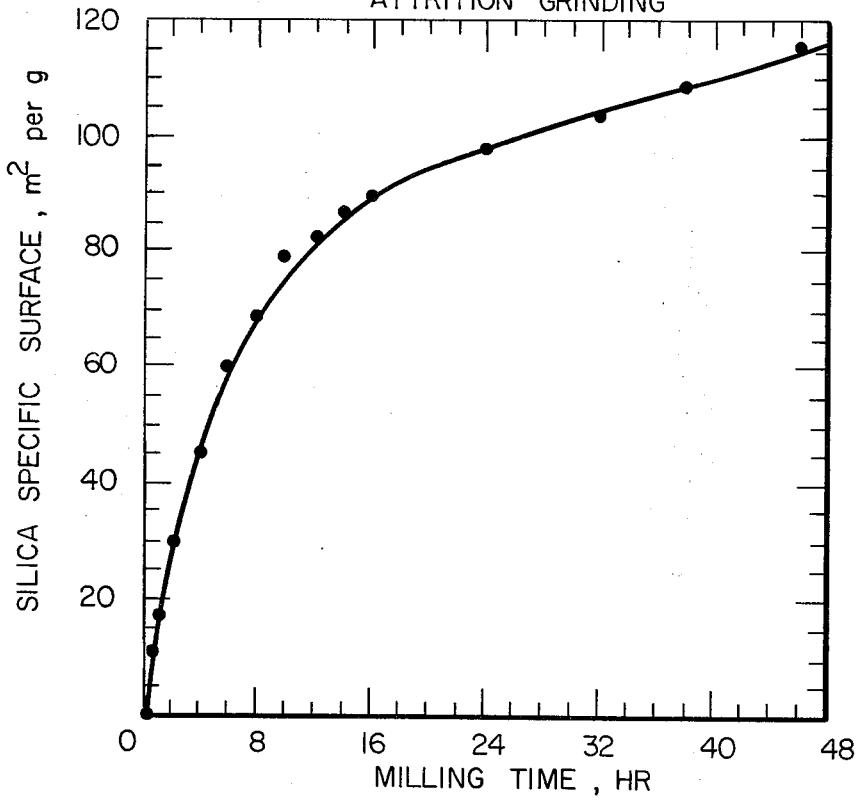
FIG. 1 – SURFACE AREA GENERATION IN SILICA BY ATTRITION GRINDING
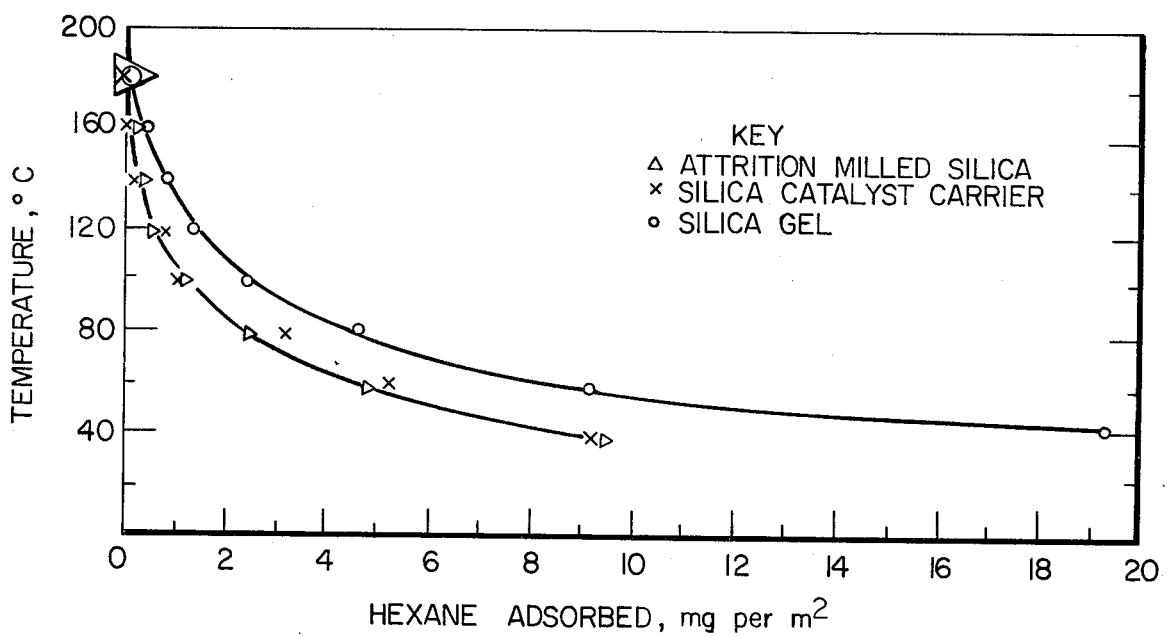
FIG. 2 – COMPARISON OF HEXANE ADSORPTION BY ATTRITION MILLED AND COMMERCIAL SILICA

CATALYSTS AND ADSORBENTS HAVING HIGH SURFACE AREA TO WEIGHT

BACKGROUND OF THE INVENTION

1. Field of the Invention

This invention pertains to catalytic and adsorbent materials having high surface area-to-weight ratios produced by attrition grinding techniques. As used herein, the term "surface area" is equivalent to "surface area-to-weight ratio".

2. Description of the Prior Art

Solid catalyst and adsorbent materials with high surface areas (>5 m$^2$/g) are conventionally made by precipitation from solution followed by calcination, or are derived from natural sources. However, certain materials cannot be prepared by the precipitation-calcination method with a sufficiently high surface area. Doped catalysts are one example, since their preparation requires temperatures sufficiently high to approach sintering and results in a lowering of the surface area. Such catalyst preparation is disclosed in Cormack et al, Journal of Catalysts, Vol. 17, pp. 220. A catalyst wherein two or more components are in solid solution comprises another example and is shown in Marcilly et al, Journal of Catalysis, Vol. 24, pp. 337–338 (1972). Certain naturally occuring crystalline minerals have a low surface area which lessens their adsorbent or catalytic activity. $\alpha$-quartz and $\alpha$-cristobalite are exemplary of such natural products.

SUMMARY OF THE INVENTION

Catalysts or adsorbents having a high surface area are prepared from naturally occuring or synthetic compositions having a relatively low surface area either as found in nature or as a result of the mode of preparation. The high surface area is developed in the compositions by an attrition grinding process.

It is an object of this invention to furnish prepared catalytic or adsorbent compositions having a high surface area from naturally occuring minerals having a low surface area.

It is a further object of this invention to furnish synthetic catalysts having a high surface area from catalytic materials wherein the high temperatures employed in their preparation destroys any high surface area-to-weight ratio, and such ratio is thereafter imparted by attrition grinding. Such catalytic materials are doped catalysts and catalysts comprising solid solutions of at least two components.

A further object of this invention is to furnish carriers for catalysts or adsorbents, said carriers having high surface areas made by attrition grinding.

Yet another object of this invention is to provide a method for preparing materials having a high surface area and useful as catalysts, adsorbents or supports for catalysts or adsorbents, wherein said high surface area is not ordinarily achievable by other means, the said method being attrition grinding.

Further objects will be apparent from the following specification and claims.

BRIEF DESCRIPTION OF THE DRAWING

FIG. 1 is a graph showing the silica surface area generated by attrition grinding; and FIG. 2 is a graph showing the variation of adsorption of n-hexane with temperature for three silica adsorbents.

DESCRIPTION OF THE INVENTION

The efficiency of a solid catalyst for catalyzing a heterogeneous chemical reaction is strongly dependent on the surface area per unit volume or weight of catalyst material since the surface is directly involved in one or more intermediate steps in the catalytic reaction. Usually the reaction rate is proportional to the specific surface (e.g. square meters per c.c. or per gram) of the catalyst material.

The weight of the catalyst and its volume (and thus the size of the reaction vessel containing the catalyst) is inversely proportional to the specific surface of the solid catalyst. Accordingly, to reduce both catalyst requirements and reaction vessel size (and therefore the cost) finely divided catalyst (high specific surface) is highly desirable. The same is true in the case of adsorbents.

Attrition milling has been shown to be a highly effective means for rapidly reducing solid materials to very small sizes with the resultant large surface areas and is described in detail in U.S. Pat. No. 3,075,710 to Feld et al. The attainment of over 100 square-meters-per-gram specific surface in 16 hours of grinding with this type of mill is not unusual. It is designed to grind by intense agitation of a grinding-medium slurry containing the powders to be ground and comprises a baffled vessel containing a concentricaly mounted impeller.

Normally, high surface area catalytic or adsorbent materials are prepared by chemical precipitation from liquid solution. At least in some cases, milling is a useful alternative method for their preparation where precipitation methods are ineffective.

The following examples illustrate the preparation of certain adsorbents and catalysts embodiments of this invention:

EXAMPLE 1

An attrition mill as in the Feld et al U.S. Pat. No. 3,075,710 was charged with 360 g minus 400 mesh silica flour ($\alpha$-quartz), 1100 g minus 14-plus 28-mesh Ottawa sand and 1700 cc water. The rotor was driven by a 1 HP motor and rotated at 1,400–1,600 rpm. FIG. 1 shows the rate of size reduction of the attrition milled silica. The milled powders were leached in concentrated HCl to remove iron contamination from the mill, washed, dried and passed through a 6-mesh screen.

Catalytic activity data for all the Examples were obtained by chemical reaction measurements. A 2.54 cm diameter Vycor glass tube was employed, heated by a 750-watt split jacket tubular electric furnace. Catalyst bed temperatures were measured by a type J thermocouple. Heating was controlled manually with a variable transformer. The 15 cc catalyst charges were held in the center of the reactor by 0.35 cm glass spheres. Dry nitrogen carrier gas was passed through a fritted glass disc and a sparger containing reactant liquid at 25° C. The saturated gas stream flowed continually to the catalyst bed.

The hexane adsorbent capacity of $\alpha$-quartz milled to 115.6 m$^2$/g (20 nanometers equivalent spherical surface) was compared with (1) a commercially available catalyst support consisting of high-surface amorphous diatomaceous earth silica having a surface area of 75.5 m$^2$/g and a particle size of minus 28-plus 48 mesh, and (2) a commercially available silica gel having a surface area of 72.5 m$^2$/g and a particle size of minus 28 plus 48 mesh. The surface areas of the adsorbents were determined using the Brunauer-Emmet-Teller nitrogen adsorption technique.

FIG. 2 shows the n-hexane absorption for the three materials. Attrition ground and amorphous catalyst carrier silica show similar hexane adsorption capacities per unit surface. The silica gel, however, exhibited a significantly higher adsorption capacity than the other two materials, attributable to a different concentration of hydroxyl groups on its surface.

EXAMPLE 2

Comparison tests of the three silicas of Example 1 as cracking catalysts for n-hexane were carried out.

During the n-hexane cracking experiments, the nitrogen flow to the sparger was held constant at 100 cc/min (measured at 25° C. and 1 atm), while the saturated gas contained the hexane at a partial pressure of 0.2 atm. The catalysts were initially subjected to nitrogen treatment for approximately 30 minutes at 550° C. prior to testing. Product gases were analyzed after 10 minutes of reactant gas flow using a gas chromotograph. Conversion data for hexane cracking were considered meaningful only between 5 and 40% of n-hexane conversion. Data below 5% were rejected because of analytical inaccuracies and above 40% to avoid errors in the measurement of intrinsic catalytic activity and catalyst deactivation due to coking caused by heat and mass transport effects and overcracking.

The following are the comparative data on the runs:

TABLE 1 n-Hexane Cracking
Gas Rate: 125 cc/min gas (80% $N_2$, 20% n-Hexane)
Pressure: 1 atm.

|  | Attrition Ground Silica | Silica Gel | Diatomaceous Earth Silica Cat. Carrier |
|---|---|---|---|
| Surface Area, m²/g: | 51.8 | 725 | 75 |
| Catalyst Charge, cc: | 15 | 15 | 15 |
| Catalyst Charge, g: | 6.86 | 9.90 | 8.00 |
| Temp., ° C. | 582 | 580 | 580 |
| Conversion % (Moles hexane converted to cracked products per 100 moles hexane feed) | 16.5 | 8.0 | 17.7 |

A typical product distribution is shown in the following table:

TABLE 2

Typical product distribution from hexane cracking

| Catalyst | Attrition Ground Silica | Diatomaceous Earth Silica Cat. Carrier |
|---|---|---|
| Temperature, ° C. | 558 | 550 |
| Conversion, % | 10.5 | 8.0 |
| Product spectrum, Mole % of total converted product |  |  |
| Methane | 18.3 | 16.2 |
| Ethane | 10.7 | 12.6 |
| Ethylene | 33.3 | 30.1 |
| Propane | 12.6 | 14.0 |
| Propylene | 20.9 | 22.7 |
| Butanes | 0.5 | 1.0 |
| Butenes | 3.7 | 3.4 |
| Pentanes | Tr | Tr |
| Iso-hexanes | Tr | Tr |

The reaction rate constant, k, was calculated in a manner similar to that shown in Miale et al "Journal of Catalysis," vol. 6, page 278 (1966). A simplified first order reaction rate constant was determined for a given temperature using the equation $$k = \left(\frac{F}{w}\right) \ln \left(\frac{1}{1-x}\right),$$

where
F = the total flow of both nitrogen and organic vapor, in cc/sec;
W = the weight of catalyst in grams;
x = fraction of hexane converted. Rate constant, k, was calculated on a weight rather than on a volume basis because of the wide variation found in catalyst bulk densities.

TABLE 3

Activities of catalysts in cracking n-hexane

|  | Attrition Ground Silica | Silica Gel | Diatomaceous Earth Silica Cat. Carrier |
|---|---|---|---|
| Rate Constant, k, cc/gm-sec | 0.157 | 0.051 | 0.145 |
| Relative Acitivity |  |  |  |
| (a) weight basis | 100 | 32 | 93 |
| (b) surface area basis | 100 | 2 | 64 |

Although the attrition milled catalyst showed a slightly lower conversion rate than the diatomaceous earth catalyst, its observed rate constant was higher because the weight of catalyst was less. Both of these catalysts were considerably more active than the silica gel. On both a weight and surface area basis the attrition ground catalyst is the most active of the three. The relative activities on a weight basis were calculated by dividing each catalyst reaction rate constant at a fixed temperature by the rate constant for the attrition ground silica and multiplying by 100. Similar calculations were made on the suface area basis.

EXAMPLE 3

A comparison test on the three catalysts of Example 1 was made in ethanol dehydration and the following data was obtained:

TABLE 4

Ethanol Dehydration
Gas Rate: 109 cc/min gas rate (92.1% $N_2$, 7.9% ethanol)
Pressure: 1 atm.

|  | Attrition Ground Silica | Silica Gel | Diatomaceous Earth Silica Cat. Carrier |
|---|---|---|---|
| Surface Area, m²g | 57.8 | 725 | 75 |
| Catalyst Charge, cc | 15 | 15 | 15 |
| Catalyst Charge, g | 6.39 | 10.34 | 7.70 |
| Temp., ° C | 241 | 245 | 235 |
| Products, mole/100 mole: ethanol feed, |  |  |  |
| ethylene | 19.1 | 61.1 | 6.75 |
| diethyl ether | 3.5 | 17.9 | 16.6 |
| ethanol | 74.1 | 2.6 | 60.0 |
| water | 22.6 | 79.0 | 23.4 |

It may thus be seen that the attrition ground silica gives about as high a conversion for ethanol dehydration as the diatomaceous-earth $SiO_2$ catalyst but lower conversion than the silica gel. However, the product distribution is different for each type of catalyst tested with the attrition ground silica giving the greatest ratio of ethylene product to ethanol dehydrated.

An important extension of this method of producing high surface area solid catalysts would be for making "doped" solid catalyst. It is often desired to dope solid catalyst material with trace quantities of another solid to promote a desired reaction. This doping is carried out at high temperature thereby precluding preparation by precipitation from aqueous solutions. However, the material could be doped at high temperature, cooled, and then attrition ground to give a doped catalyst having high surface areas. Manganese doped aluminum oxide is an example of such a material. Catalysts having components in solid solution, such as $Al_2O_3$-$Cr_2O_3$ catalysts treated at high temperatures, normally would have low surface areas. Attrition grinding provides a method for producing these catalysts with surface area for higher than attained after the high temperature treatment.

As is apparent from FIG. 1, the surface area is a function of the milling time. Useful catalyst or adsorbent surface area/gram can be as low as 0.5 m/g for some purposes. In general a surface area of 30 $m^2/g$ will give useful results. In the case of silica a range of from about 50 to about 116 $m^2/g$ will be desirable. However, if desired, or as may be required in a particular situation, the surface area may be as high as 116 $m^2/g$ or even larger. In general, the larger the surface area the lesser amount of catalyst or adsorbent and the smaller size vessel needed. However, this is counterbalanced by the greater costs involved in grinding to a higher surface area.

The foregoing is considered as illustrating the principles of the invention. It is apparent that numerous modifications and applications falling within its scope will occur to persons skilled in the art.

What is claimed:

1. A method for imparting catalytic activity and adsorption capacity to a crystalline silica which comprises subjecting said crystalline silica to attrition grinding for a time sufficient to produce a surface area of at least 30$m^2/g$.

2. The method of claim 1 wherein the silica is a naturally occurring crystalline silica.

3. The method of claim 2 wherein the crystalline silica is $\alpha$-quartz.

4. The method of claim 2 wherein the crystalline silica is $\alpha$-cristobalite.

* * * * *